(12) United States Patent
Kaito et al.

(10) Patent No.: US 8,269,194 B2
(45) Date of Patent: Sep. 18, 2012

(54) COMPOSITE FOCUSED ION BEAM DEVICE, AND PROCESSING OBSERVATION METHOD AND PROCESSING METHOD USING THE SAME

(75) Inventors: Takashi Kaito, Chiba (JP); Junichi Tashiro, Chiba (JP); Yasuhiko Sugiyama, Chiba (JP); Kouji Iwasaki, Chiba (JP); Toshiaki Fujii, Chiba (JP); Kazuo Aita, Chiba (JP); Takashi Ogawa, Chiba (JP)

(73) Assignee: SII NanoTechnology Inc. (JP)

( * ) Notice: Subject to any disclaimer, the term of this patent is extended or adjusted under 35 U.S.C. 154(b) by 204 days.

(21) Appl. No.: 12/733,089

(22) PCT Filed: Aug. 6, 2008

(86) PCT No.: PCT/JP2008/064122
§ 371 (c)(1),
(2), (4) Date: Mar. 19, 2010

(87) PCT Pub. No.: WO2009/020150
PCT Pub. Date: Feb. 12, 2009

(65) Prior Publication Data
US 2010/0176296 A1 Jul. 15, 2010

(30) Foreign Application Priority Data
Aug. 8, 2007 (JP) ................................. 2007-207097

(51) Int. Cl.
*H01J 49/00* (2006.01)
(52) U.S. Cl. ............. 250/492.21; 250/492.1; 250/492.3; 250/493.1

(58) Field of Classification Search .................. 250/306, 250/309, 492.21, 423 R
See application file for complete search history.

(56) References Cited

U.S. PATENT DOCUMENTS

| | | | | |
|---|---|---|---|---|
| 4,874,460 A | * | 10/1989 | Nakagawa et al. | 216/61 |
| 5,023,453 A | * | 6/1991 | Adachi et al. | 850/9 |
| 5,149,973 A | * | 9/1992 | Morimoto | 250/492.2 |
| 5,306,663 A | * | 4/1994 | Morimoto | 438/641 |
| 5,504,340 A | * | 4/1996 | Mizumura et al. | 250/492.21 |
| 5,525,806 A | * | 6/1996 | Iwasaki et al. | 250/492.21 |
| 5,583,344 A | * | 12/1996 | Mizumura et al. | 250/492.21 |
| 5,825,035 A | * | 10/1998 | Mizumura et al. | 250/423 R |

OTHER PUBLICATIONS

Abstract, publication No. 02-123749, publication date May 11, 1990.

* cited by examiner

*Primary Examiner* — Jack Berman
*Assistant Examiner* — Johnnie L Smith
(74) *Attorney, Agent, or Firm* — Adams & Wilks

(57) ABSTRACT

A composite focused ion beam device has a sample stage for supporting a sample, a first ion beam irradiation system that irradiates a first ion beam for processing the sample, and a second ion beam irradiation system that irradiates a second ion beam for processing or observing the sample. The first ion beam irradiation system has a liquid metal ion source that generates first ions for forming the first ion beam. The second ion beam irradiation system has a gas field ion source that generates second ions for forming the second ion beam. The first ion beam irradiated by the first ion beam irradiation system has a first beam diameter and the second ion beam irradiated by the second ion beam irradiation system has a second beam diameter smaller than the first beam diameter. The first and second ion beam irradiation systems are disposed relative to the sample stage so that axes of the first and second ion beams are orthogonal to a tilt axis of the sample stage.

19 Claims, 12 Drawing Sheets

COMPOSITE FOCUSED ION BEAM DEVICE, AND PROCESSING OBSERVATION METHOD AND PROCESSING METHOD USING THE SAME

CROSS-REFERENCE TO RELATED APPLICATIONS

This application is a U.S. national stage application of copending International Application No. PCT/JP2008/064122, filed Aug. 6, 2008, claiming a priority date of Aug. 8, 2007, and published in the non-English language.

BACKGOUND OF THE INVENTION

1. Technical Field

The present invention relates to a composite focused ion beam device, and a processing observation method and a processing method using the same.

Priority is claimed on Japanese Patent Application No. 2007-207097, the content of which is incorporated herein by reference.

2. Background Art

Conventionally, as a processing observation device used for evaluation of a semiconductor process, a device including a gallium ion beam irradiation system for process and an electron beam irradiation system for observation is known (for example, see Patent Citation 1).

According to the processing observation device described in Patent Citation 1, processing of samples using a focused ion beam and observation of samples using a Scanning Electron Microscope (SEM) are possible. However, recently, there is a need for high performance in such a processing observation device, and high resolution of an SEM, which is an observation device, is required. In order to perform high-resolution observation using an SEM, a beam diameter needs to be narrowed, but an electron beam is influenced by diffraction aberration and thus a Working Distance (WD) should be small in order to decrease the beam diameter. In this case, since an ion beam lens barrel is disposed in the vicinity of the sample, there is a restriction in design for avoiding interference between lens barrels or in the shape or disposition of a sample.

In addition, a focused ion beam in which a liquid gallium is used in an ion source may be irradiated to the sample so as to obtain a sample image (SIM image). However, the sample may be sputtered by the irradiation of the ion beam and thus the state thereof may be changed.

Patent Citation 1: Japanese Unexamined Patent Application Publication No. 2-123749

SUMMARY OF THE INVENTION

The present invention is contrived to solve the above-mentioned problems. An object of the present invention is to provide a composite focused ion beam device capable of realizing high-resolution observation or minute processing, and a processing observation method and a processing method using the same.

In order to solve the above-described problems, the following means are employed.

In order to solve the above-described problems, there is provided a composite focused ion beam device including: a first ion beam irradiation system including a liquid metal ion source for generating a first ion; and a second ion beam irradiation system including a gas field ion source for generating a second ion, wherein a beam diameter of the second ion beam emitted from the second ion beam irradiation system is less than that of the first ion beam emitted from the first ion beam irradiation system.

According to this configuration, since two types of ion beam irradiation systems are included, it is possible to process the sample using one ion beam irradiation system while observing the sample using the other ion beam irradiation system. In particular, since the beam diameter of the second ion beam irradiation system including the gas field ion source can be narrowed to 1 nm or less, high-resolution observation is possible.

Since the ion beam is used unlike the SEM, the influence of diffraction aberration is substantially negligible. Accordingly, since the beam diameter can be narrowed even when the Working Distance (WD) is large, interference between ion beam irradiation systems hardly occurs and a degree of freedom in the design of a device is increased.

A mass of the second ion may be less than that of the first ion. Accordingly, since the second ion beam irradiation system for emitting an ion having a small mass is used in an observation device, it is possible to suppress sample sputtering by the irradiation of the ion beam and thus to perform super-high-resolution observation using an extremely minute beam diameter.

The first ion beam irradiation system and the second ion beam irradiation system may be disposed such that the first ion beam and the second ion beam cross at an acute angle.

By such disposition of the first and second ion beam irradiation systems, it is possible to obtain a composite focused ion beam device which can be suitably used for an application for processing a sample while observing the sample.

A sample pedestal for supporting a sample to which the first and second ion beams are irradiated may be included, and the second ion beam irradiation system may be disposed on the vertical upper side of the sample pedestal and the first ion beam irradiation system may be disposed obliquely to a vertical direction.

By disposing the second ion beam irradiation system on the vertical upper side of the sample pedestal, it is possible to more easily perform processing and observation using the second ion beam irradiation system having a small beam diameter and requiring high-precision position control.

The first and second ion beam irradiation systems may be disposed such that the first and second ion beams are substantially orthogonal to each other.

By this configuration, since the ion beam can be vertically irradiated from one ion beam irradiation system to the processed portion of the sample using the other ion beam irradiation system, in particular, it is possible to obtain a configuration suitable for an application requiring observation during processing.

The gas field ion source may include an emitter, an extraction electrode having an opening facing a front end of the emitter, and a gas supply unit for supplying gas which becomes the second ion.

By the gas field ion source having this configuration, it is possible to stably form an ion beam having a small beam diameter.

The second ion may be a helium ion.

By this configuration, a composite focused ion beam device including the second ion beam irradiation system capable of obtaining a sample image without significant sample sputtering is obtained. As the second ion, a neon ion may be used.

The first ion beam irradiation system and the second ion beam irradiation system may be disposed such that the first ion beam and the second ion beam cross at 45 degrees to 60 degrees.

By this configuration, it is possible to improve processing efficiency when a TEM sample is manufactured.

The axes of the first ion beam irradiation system and the second ion beam irradiation system may be orthogonal to a stage tilt axis and the axis of the third ion beam irradiation system and the stage tilt axis may be located in the same plane.

By such disposition, it is possible to easily set an angle of the ion beam irradiated from each of the ion beam irradiation systems with the sample and, as a result, to improve the processing property of the sample.

A detection device for detecting at least one of a secondary charged particle generated or reflected from the sample by the irradiation of the first ion or the second ion and a charged particle transmitted through the sample and an image display device for displaying an image of the sample based on the output of the detection device may be included.

By this configuration, a configuration in which the observation of a sample image is possible by the irradiation of the ion beam is obtained.

The detection device may include a first ion detector for detecting a secondary ion generated by the irradiation of the first ion generated from the first ion beam irradiation system and a second ion detector for detecting a reflection ion reflected by collision of the second ion, which is generated from the second ion beam irradiation system and lighter than the first ion, with the sample.

By this configuration, it is possible to acquire an image obtained from a secondary ion and an image obtained from a reflection ion. To this end, for example, during processing, it is possible to simultaneously acquire the image of the sample surface of the processed portion of the sample and the image of the sample section of the processed portion.

The detection device may include at least one of an electron detector, an ion detector, and a transmitted charged particle detector. That is, devices for detecting at least one of a secondary electron, a secondary ion, a scattered ion, and a transmitted charged particle generated from the sample by the irradiation of the ion beam may be included.

A gas gun for supplying functional gas for deposition or etching to the vicinity of the sample to which the first and second ion beams are irradiated may be included.

According to this configuration, it is possible to obtain a composite focused ion beam device capable of rapidly and easily performing the formation of a structure by gas assist deposition and processing of the sample by gas assist etching.

There is provided a processing observation method of irradiating an ion beam to a sample so as to perform processing and observation, the processing observation method including the steps of: irradiating a first ion beam from a first ion beam irradiation system including a liquid metal ion source for generating a first ion to the sample so as to process the sample; and irradiating a second ion beam from a second ion beam irradiation system, which includes a gas field ion source for generating a second ion and emits an ion beam having a beam diameter less than that of the first ion beam, to the sample so as to observe the sample.

According to this method, it is possible to rapidly and efficiently perform the processing of the sample using the first ion beam irradiation system having large beam current and to perform high-resolution observation while avoiding damage of the sample using the second ion beam irradiation system having a small beam diameter.

In addition, an ion having a mass less than that of a first ion may be used as a second ion. Accordingly, it is possible to prevent sample sputtering when the second ion beam is irradiated so as to observe the sample and to obtain an accurate observed result without changing a sample state.

The step of irradiating the first ion beam so as to process the sample and the step of irradiating the second ion beam so as to observe the sample may be simultaneously performed.

According to this configuration, when the processing is performed by irradiating the first ion beam, it is possible to perform the observation of the processed portion in real time and to improve processing precision.

After the step of irradiating the first ion beam so as to process the sample, a step of irradiating a third ion beam from a third ion beam irradiation system including a plasma type gas ion source for generating a third ion to the sample may be included. As the third ion beam, a low-acceleration argon ion beam of 1 keV or less is suitable.

According to this method, if a thin section of a TEM sample is manufactured, it is possible to remove a damaged layer generated in the processing of the thin section using the first ion beam by the irradiation of the third ion beam.

A step of irradiating the second ion beam to the sample while gas is supplied to an ion beam irradiation position of the sample so as to process the sample may be included.

If the sample is processed using the second ion beam irradiation system, since minute processing is possible as compared with the case where the first ion beam irradiation system is used, it is possible to easily perform minute high-precision processing by the combination of the processing using the first ion beam irradiation system and the processing using the second ion beam irradiation system and to perform a higher degree of analysis.

There is provided a processing method of irradiating an ion beam to a sample so as to perform processing, the processing method including the steps of: irradiating a first ion beam from a first ion beam irradiation system including a liquid metal ion source for generating a first ion to the sample so as to process the sample; and irradiating a second ion beam from a second ion beam irradiation system, which includes a gas field ion source for generating a second ion and emits an ion beam having a beam diameter less than that of the first ion beam, to the sample so as to process the sample.

According to this processing method, since the processing of the sample using the second ion beam having a relatively small beam diameter is performed, it is possible to perform the processing of a minute region as well as the processing of the sample using the first ion beam irradiation system. Accordingly, according to this processing method, it is possible to efficiently and rapidly perform high-precision processing.

There is provided a processing method of irradiating an ion beam to a sample so as to perform processing, the processing method comprising the steps of: irradiating a first ion beam from a first ion beam irradiation system including a liquid metal ion source for generating a first ion to the sample so as to process the sample; and irradiating a second ion beam from a second ion beam irradiation system, which includes a gas field ion source for generating a second ion and emits an ion beam having a beam diameter less than that of the first ion beam, to at least a portion of a processed portion by the irradiation of the first ion beam of the sample so as to perform after-processing with respect to the sample.

According to this processing method, after the first ion beam is irradiated so as to process the sample, the second ion beam having a relatively small beam diameter may be irradiated to the processed portion so as to perform after-processing. That is, since the finishing processing can be performed by the irradiation of the second ion beam after rough processing is performed by the irradiation of the first ion beam, it is possible to efficiently perform high-precision processing and to remove a damaged portion generated by the irradiation of the first ion beam.

The step of irradiating the first ion beam to the sample to process the sample and the step of further irradiating the second ion beam to at least a portion of a processed portion of the sample by the irradiation of the first ion beam so as to perform the after-processing with respect to the sample may be simultaneously performed.

In this case, it is possible to simultaneously perform the rough processing by the irradiation of the first ion beam and the finishing processing by the irradiation of the second ion beam and to further improve processing efficiency.

A step of irradiating the second ion beam to the sample while gas is supplied to an ion beam irradiation position of the sample so as to process the sample may be included.

By this processing method, it is possible to improve processing efficiency using the second ion beam irradiation system.

According to the present invention, it is possible to provide a composite focused ion beam device capable of performing super-high-resolution observation or super-high-precision processing which is impossible by a conventional composite focused ion beam device or composite charged particle beam device.

The composite focused ion beam device according to the present invention is characterized by a He ion beam of a gas field ion source which can obtain super-high resolution even if a long WD is used instead of an SEM. Accordingly, super-high-resolution section observation superior to the SEM can be realized.

According to the present invention it is possible to provide a processing observation method capable of performing super-high-resolution observation superior to the conventional method while processing a sample.

EXPLANATION OF REFERENCE SYMBOLS

10: FIRST ION BEAM IRRADIATION SYSTEM
10A: FIRST ION BEAM
11: GAS GUN
14: SAMPLE PEDESTAL
15: SAMPLE HOLDER
16: SAMPLE STAGE
18: SECONDARY CHARGED PARTICLE DETECTOR
19: TRANSMITTED CHARGED PARTICLE DETECTOR
20: SECOND ION BEAM IRRADIATION SYSTEM
20A: SECOND ION BEAM
21: GAS FIELD ION SOURCE
21a: ION GENERATION CHAMBER
25: ION OPTICAL SYSTEM
26: GAS SUPPLY SOURCE
30: CONTROL DEVICE
34: LIQUID METAL ION SOURCE
35: ION OPTICAL SYSTEM
38: DISPLAY DEVICE
40: THIRD ION BEAM IRRADIATION SYSTEM
40A: THIRD ION BEAM
44: PLASMA TYPE GAS ION SOURCE
45: ION OPTICAL SYSTEM
Wa: SAMPLE
Wb: SAMPLE
100, 100A, 200: COMPOSITE FOCUSED ION BEAM DEVICE

DETAILED DESCRIPTION OF THE EMBODIMENTS

Hereinafter, the embodiments of a composite focused ion beam device of the present invention will be described with reference to the drawings.

Figure 1:
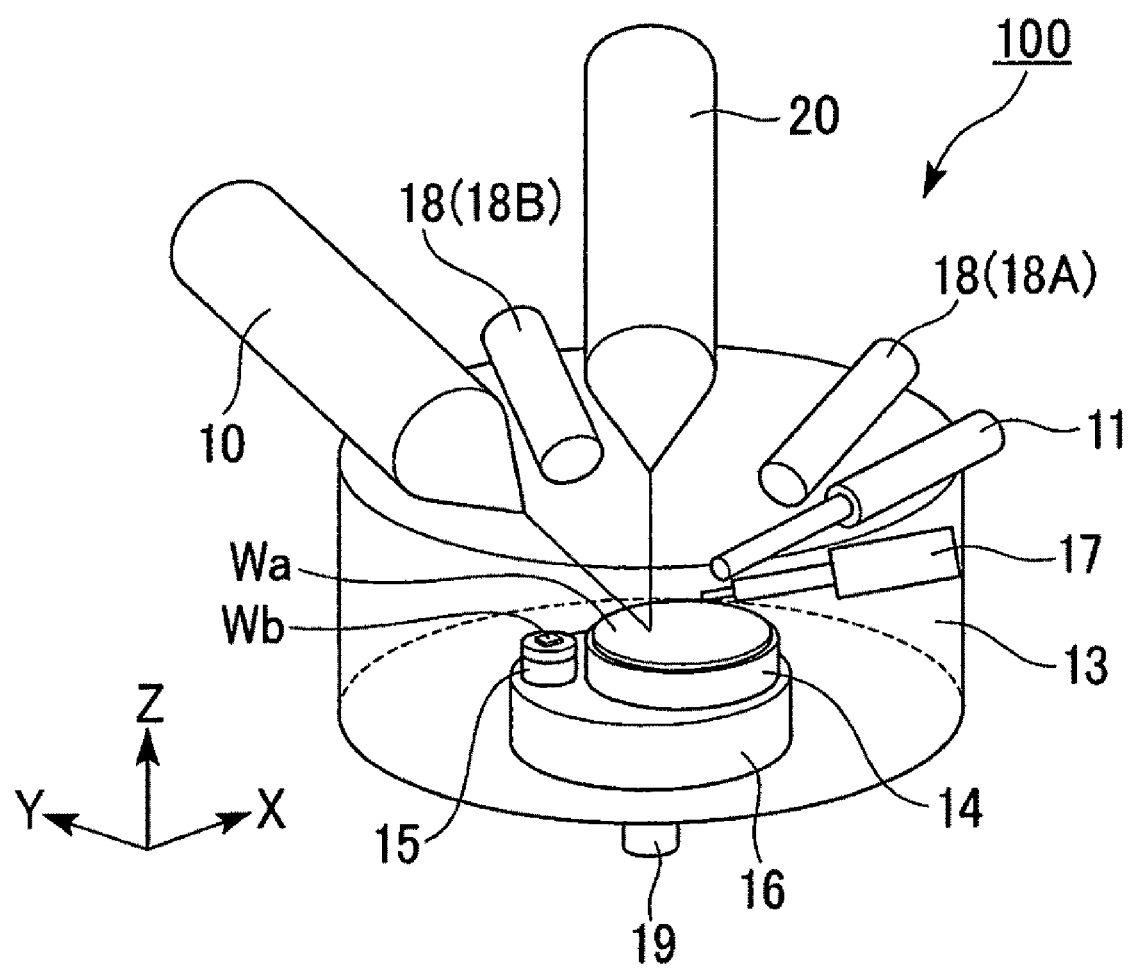
FIG. 1 is a schematic configuration diagram of a composite focused ion beam device according to a first embodiment.
Figure 2:
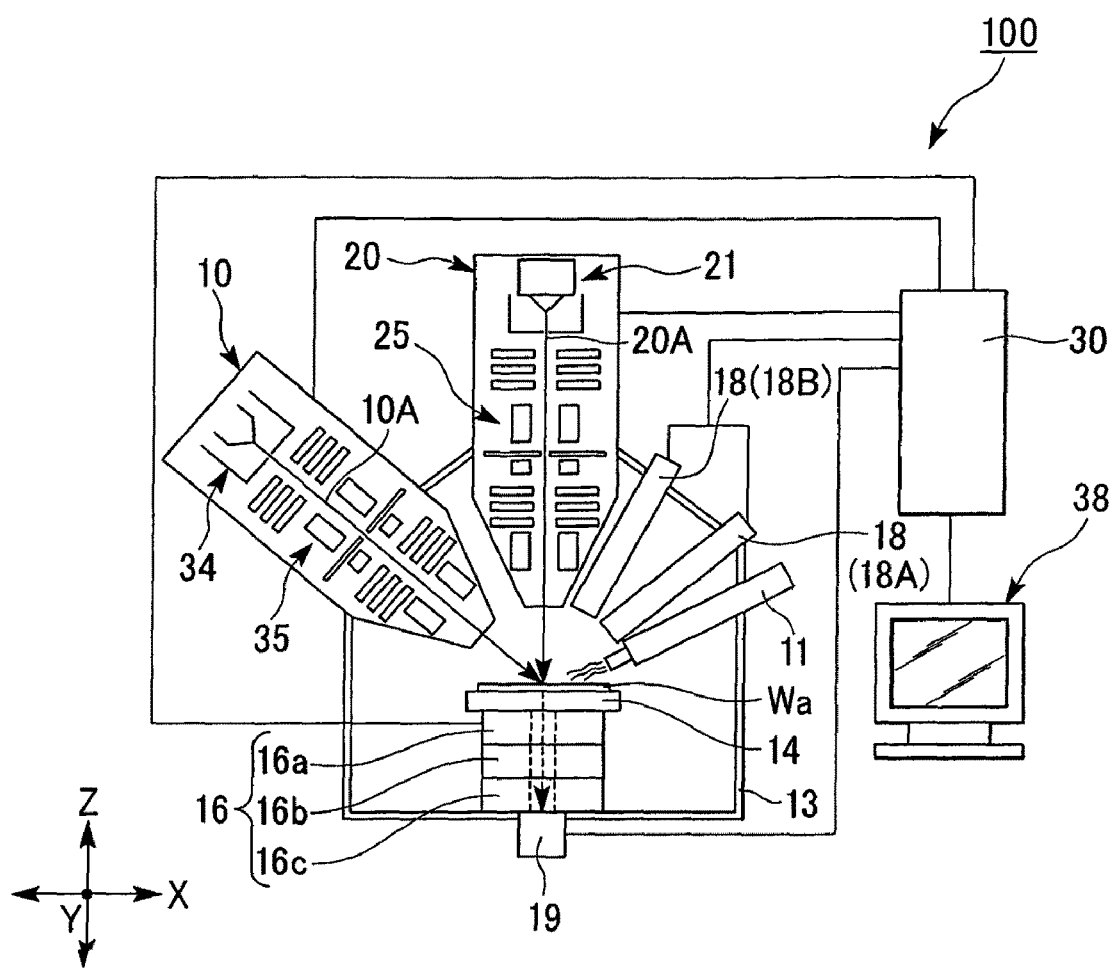
FIG. 2 is a schematic cross-sectional view of the composite focused ion beam device according to the first embodiment.

FIG. 1 is a schematic configuration diagram of a composite focused ion beam device according to the present embodiment. FIG. 2 is a schematic cross-sectional view of the composite focused ion beam device 100.

As shown in FIGS. 1 and 2, the composite focused ion beam device 100 according to the present invention includes a vacuum chamber 13, a first ion beam irradiation system 10, a second ion beam irradiation system 20, a sample stage 16, a manipulator 17, a secondary charged particle detector 18, a transmitted charged particle detector 19, and a gas gun 11. The inside of the vacuum chamber 13 can be depressurized to a predetermined vacuum degree and some or all of the above components are disposed in the vacuum chamber 13.

In the present embodiment, each of the first ion beam irradiation system 10 and the second ion beam irradiation system 20 has a focused ion beam lens barrel and irradiates a focused ion beam (a first ion beam 10A or a second ion beam 20A) to a sample (an object to be processed or an object to be observed) on a sample stage 16 disposed in the vacuum chamber 13. The first ion beam 10A and the second ion beam 20A cross each other at an acute angle and are irradiated at the same position on the sample disposed at the crossing position.

The first ion beam irradiation system 10 and the second ion beam irradiation system 20 are disposed such that the first ion beam 10A and the second ion beam 20A cross each other at 45 degrees to 60 degrees. In other words, the first ion beam irradiation system 10 and the second ion beam irradiation system 20 are disposed such that an opened angle θa between the axes thereof becomes 45 degrees to 60 degrees.

The first ion beam irradiation system 10 has a liquid metal ion source 34 using liquid gallium or the like and an ion optical system 35 for forming ions emitted from the liquid metal ion source 34 into an ion beam and emitting the ion beam.

As ions configuring the liquid metal ion source 34, for example, gallium ions (Ga+) are used. The liquid metal ion source 34 is connected to an ion source control power source (not shown). In addition, the ion source control power source may apply an acceleration voltage and an extraction voltage so as to accelerate extracted ions and to emit the ion beam.

The ion optical system 35 includes, for example, a condenser lens for focusing an ion beam, a diaphragm for narrowing the ion beam, an aligner for adjusting an optical axis of the ion beam, an objective lens for focusing the ion beam to a sample, and a deflector for scanning the ion beam on the sample, sequentially from the liquid metal ion source 34.

The second ion beam irradiation system 20 includes a gas field ion source 21 for generating and emitting a second ion and an ion optical system 25 for forming the second ions emitted from the gas field ion source 21 into a focused ion beam (second ion beam 20A).

The ion optical system 25 has the same basic configuration as the ion optical system 35 included in the first ion beam irradiation system 10 and includes, for example, a condenser lens for focusing an ion beam, a diaphragm for narrowing the ion beam, an aligner for adjusting an optical axis of the ion beam, an objective lens for focusing the ion beam to a sample, and a deflector for scanning the ion beam on the sample.

Figure 3:
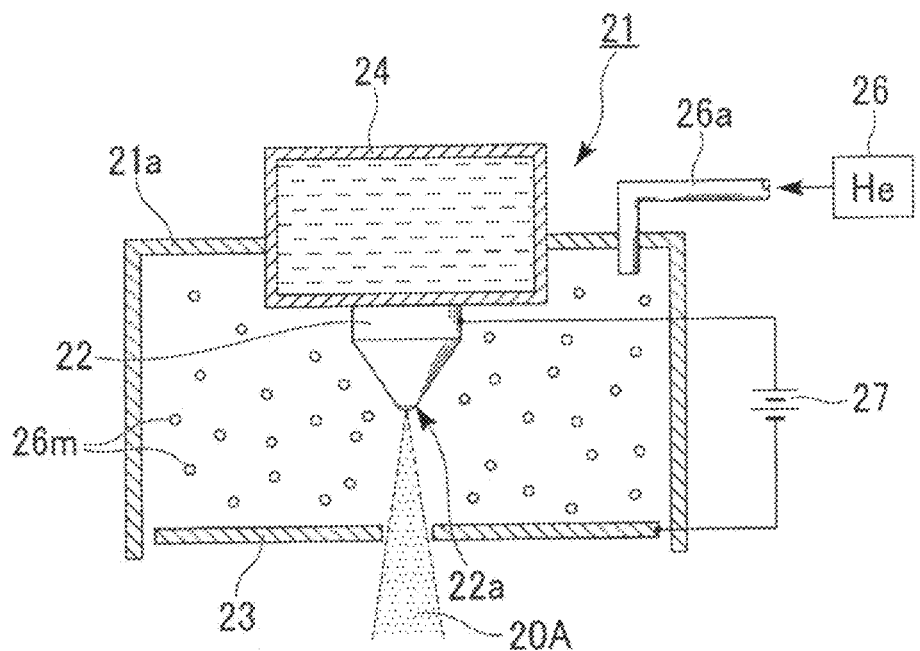
FIG. 3 is a cross-sectional view of a field emission type ion source.

FIG. 3 is a cross-sectional view of the gas field ion source 21.

As shown in FIG. 3, the gas field ion source 21 includes an ion generation chamber 21a, an emitter 22, an extraction electrode 23, and a cooling device 24. The cooling device 24 is disposed on a wall of the ion generation chamber 21a and a needle-like emitter 22 is mounted on a surface of the cooling device 24 facing the ion generation chamber 21a. The cooling device 24 cools the emitter 22 by a cooling medium such as liquid nitrogen or the like contained therein. In addition, the extraction electrode 23 having an opening 23a is disposed at a position facing a tip 22a of the emitter 22 in the vicinity of an opened end of the ion generation chamber 21a.

The inside of the ion generation chamber 21a is maintained in a desired high vacuum state using an exhauster (not shown). A gas supply source 26 is connected to the ion generation chamber 21a via a gas introduction pipe 26a and a small amount of gas (for example, helium gas) is supplied into the ion generation chamber 21a.

In addition, the gas supplied from the gas supply source 26 to the gas field ion source 21 is not limited to helium gas and gas such as neon, argon or xenon may be used. In addition, plural types of gas may be configured to be supplied from the gas supply source 26 such that the gas type is changed according to the use of the second ion beam irradiation system 20.

The emitter 22 is a member obtained by coating a needle-like base formed of tungsten or molybdenum with noble metal such as platinum, palladium, iridium, rhodium or gold, and the tip 22a thereof is sharpened at an atomic level so as to have a pyramid shape. In addition, the emitter 22 is maintained at a low temperature of about 78 K or less by the cooling device 24 during operation of the ion source. A voltage is applied between the emitter 22 and the extraction electrode 23 by a power source 27.

If the voltage is applied between the emitter 22 and the extraction electrode 23, a significantly large electric field is generated in the sharpened tip 22a and helium atoms 26m polarized and attracted to the emitter 22 lose electrons so as to become helium ions (second ions) by tunneling at a position having a high electric field on the surface of the tip 22a (electric field ionization). These helium ions are repulsed against the emitter 22 held at a positive potential and shoot out to the extraction electrode 23 such that the helium ions emitted from the opening 23a of the extraction electrode 23 to the ion optical system 25 configure the ion beam.

Since the tip 22a of the emitter 22 has an extremely sharpened shape and the helium ions shoot out from the tip 22a, the energy distribution width of the ion beam emitted from the gas field ion source 21 is extremely narrow and an ion beam having a small beam diameter and high luminance can be obtained, compared with the plasma type gas ion source or the liquid metallic ion source 34.

In addition, if the voltage applied to the emitter 22 is extremely large, the constituent element (tungsten or platinum) of the emitter 22 flies toward the extraction electrode 23 together with the helium ions and thus the voltage applied to the emitter 22 at the time of operation (at the time of ion beam radiation) is maintained at a voltage for preventing the constituent element of the emitter 22 itself from shooting out.

Meanwhile, the shape of the tip 22a can be adjusted by adjusting the constituent element of the emitter 22. For example, an element located at the uppermost end of the tip 22a is intentionally removed so as to widen a region for ionizing the gas such that the diameter of the ion beam can be increased.

In addition, since the emitter 22 can be heated such that the noble metal element of the surface thereof is rearranged without shooting out, the sharpened shape of the tip 22a which thickens with use can be recovered.

Returning to FIGS. 1 and 2, the sample stage 16 movably supports a sample pedestal 14 and a sample holder 15. A sample Wa (for example, a semiconductor wafer or the like) is laid on the sample pedestal 14, and a minute sample Wb manufactured from the sample Wa is laid on the sample holder 15. The sample stage 16 can displace the sample pedestal 14 and the sample holder 15 in five axes. That is, an XYZ movement mechanism 16b for moving the sample pedestal 14 along an X axis and a Y axis which are parallel to a horizontal plane and are orthogonal to each other and a Z axis orthogonal to the X axis and the Y axis, a rotation mechanism 16c for rotating the sample pedestal 14 around the Z axis, and a tilt mechanism 16a for rotating the sample pedestal 14 around the X axis (or the Y axis) are included. The sample stage 16 displaces the sample pedestal 14 in the five axes such that a specific position of the sample Wa (sample Wb) becomes a position where the ion beam is irradiated.

The inside of the vacuum chamber 13 can be depressurized to a predetermined vacuum degree, and the manipulator 17, the secondary charged particle detector 18, the transmitted charged particle detector 19 and the gas gun 11 are provided in the vacuum chamber 13.

The manipulator 17 supports the sample Wb manufactured from the sample Wa. By relatively moving the manipulator 17 and the sample holder 15 in a state in which the sample Wb is supported, the sample Wb is transported from the sample pedestal 14 to the sample holder 15. During transportation, the sample stage 16 may be driven in a state in which the manipulator 17 is fixed such that the sample holder 15 is moved to a position where the sample Wb is supported, and the manipulator 17 may be moved so as to transport the sample Wb.

The secondary charged particle detector 18 detects the secondary electrons, the secondary ions, or the reflection ions generated or reflected from the sample Wa or the sample Wb when the focused ion beam is irradiated from the first ion beam irradiation system 10 or the second ion beam irradiation system 20 to the sample Wa or the sample Wb. In addition, the transmitted charged particle detector 19 detects the ions transmitted through the sample Wa or the sample Wb when the focused ion beam is irradiated from the second ion beam irradiation system 20 to the sample Wa or the sample Wb.

In this embodiment, the secondary charged particle detector 18 includes a first ion detector 18A for detecting the secondary ions generated by the irradiation of the first ions generated from the first ion beam irradiation system 10 and a second ion detector 18B for detecting the reflection ions reflected by the collision of the second ions, which is generated from the second ion beam irradiation system and lighter than the first ions, with the sample. The degree of freedom of the disposition of the first ion detector 18A is high because the secondary ions generated by the irradiation of the first ions are radiated over a wide range. In contrast, the second ion detector 18B is preferably disposed in the vicinity of the beam lens barrel of the first ion beam irradiation system 10 because the radiation angle of the reflection ions reflected by collision with the samples Wa and Wb is decided to a certain extent.

The gas gun 11 emits predetermined gas such as gas assist etching gas or gas assist deposition gas to the samples Wa and Wb. In addition, the first ion beam 10A or the second ion beam 20A is irradiated to the samples Wa and Wb while supplying the etching gas from the gas gun 11 such that the etching rate of the sample using the ion beam can be increased. Meanwhile, if the ion beam is irradiated to the samples Wa and Wb while supplying the deposition gas from the gas gun 11, it is possible to form a deposit of an insulating material or metal on the samples Wa and Wb.

The composite focused ion beam device 100 includes a control device 30 for controlling the components configuring the device. The control device 30 is connected to the first ion beam irradiation system 10, the second ion beam irradiation system 20, the secondary charged particle detector 18, the transmitted charged particle detector 19, and the sample stage 16. A display device 38 for displaying the sample Wa and the sample Wb as an image based on the output from the secondary charged particle detector 18 or the transmitted charged particle detector 19 is included.

The control device 30 comprehensively controls the composite focused ion beam device 100, converts the secondary charged particles or the transmitted charged particles detected by the secondary charged particle detector 18 or the transmitted charged particle detector 19 into a luminance signal so as to generate image data, and outputs the image data to the display device 38. Accordingly, the display device 38 can display the sample image as described above.

In addition, the control device 30 drives the sample stage 16 based on an instruction of software or input of an operator so as to adjust the position or the attitude of the sample Wa or the sample Wb. Therefore, the irradiation position or the irradiation angle of the ion beam on the sample surface can be adjusted. For example, the sample stage 16 can be driven by interlocking with the switching operation of the first ion beam irradiation system 10 and the second ion beam irradiation system 20 such that the sample Wa or the sample Wb is moved or tilted.

In the composite focused ion beam device 100 according to the present embodiment having the above configuration, the mass of the second ions (helium ions) emitted from the second ion beam irradiation system 20 is less than that of the first ion (gallium ions) emitted from the first ion beam irradiation system 10. To this end, even when the second ion beam 20A is irradiated onto the sample Wa or the sample Wb, the sample will not sputter easily and an ion beam irradiation system suitable for secondary charged particle image observation of the sample Wa or the sample Wb is obtained.

In addition, in the second ion beam irradiation system 20, since a source size is 1 nm or less and the energy spread of the ion beam is 1 eV or less, the beam diameter can be narrowed to 1 nm or less.

In order to obtain the beam diameter of 1 nm or less, WD should be set to 1 to 2 mm or less in order to avoid the influence of diffraction aberration in the Scanning Electron Microscope (SEM), but WD is extremely hard to set to 5 mm or less by mechanical interference between lens barrels in a composite device having a plurality of beam irradiation systems.

In contrast, in the second ion beam 20A, since the momentum of the used helium ions is significantly greater than that of the electron used in the SEM and the de Broglie wave length is significantly small, the diffraction effect is negligibly small.

Accordingly, since the diffraction aberration is negligible in the second ion beam, the small beam diameter can be obtained even when WD lengthens, and high-resolution observation and measurement of a large sample is possible.

In addition, in the second ion beam 20A, since the interaction volume of the sample extends from the surface in a depth direction and the spread of the sample surface in the surface direction is decreased, a sample image to which information about the position where the ion beam is irradiated is accurately applied can be obtained and thus the charge-up of the sample can be suppressed. In addition, since the momentum of the helium ions is significantly greater than that of the electrons, a larger amount of secondary electrons are emitted from the sample surface.

Accordingly, the second ion beam 20A is irradiated to the sample so as to perform the secondary charged particle image observation such that a sample image with high resolution or high contrast can be obtained.

The second ion beam irradiation system 20 can emit an ion beam having a beam diameter less than that of the first ion beam irradiation system 10. By using the second ion beam 20A having a small beam diameter, minute processing (etching, deposition) is possible compared with the case where the sample is processed using the first ion beam 10A.

In addition, if the second ion beam 20A is configured by the helium ions, the sample is hardly etched by only irradiating the ion beam to the sample, but the sample can be processed at a practical speed by irradiating the second ion beam 20A to the sample while etching assist gas is supplied from the gas gun 11. In addition, if the second ion beam 20A is configured with neon ions or argon ions having a mass greater than that of the helium ions, processing efficiency can be improved.

In the composite focused ion beam device 100 of the present embodiment, since two ion beam irradiation systems having different processing dimensions are included, the ion beam irradiation systems are selected or combined according to the use thereof.

In detail, a combination in which the first ion beam irradiation system 10 having a large beam diameter is mainly used for processing and the second ion beam irradiation system 20 which has a small beam diameter and can avoid the sample sputtering is mainly used for observation may be exemplified as a first combination.

A combination in which the first ion beam irradiation system 10 is used for rough processing of the sample and the second ion beam irradiation system 20 is used for high-precision processing may be exemplified as a second combination.

In the present embodiment, as shown in FIG. 2, the second ion beam irradiation system 20 is disposed on the vertical upper side of the sample stage 16 so as to irradiate the second ion beam 20A to the sample Wa or the sample Wb in a vertical direction. Meanwhile, the first ion beam irradiation system 10 is disposed obliquely to the vertical direction so as to irradiate the first ion beam 10A to the sample Wa or the sample Wb in an oblique direction.

In the configuration in which the second ion beam 20A formed of the helium ions is emitted along the vertical direction, high-precision stage control is facilitated at the time of observation or processing and, more particularly, desired precision of the processing using the second ion beam 20A can be easily obtained.

In addition, the disposition of the first ion beam irradiation system 10 and the second ion beam irradiation system 20 is not limited to that shown in FIG. 2 and various disposition forms may be employed. For example, in FIG. 2, the second ion beam irradiation system 20 may be disposed so as to obliquely irradiate the second ion beam 20A to the sample Wa or the sample Wb.

Figure 4:
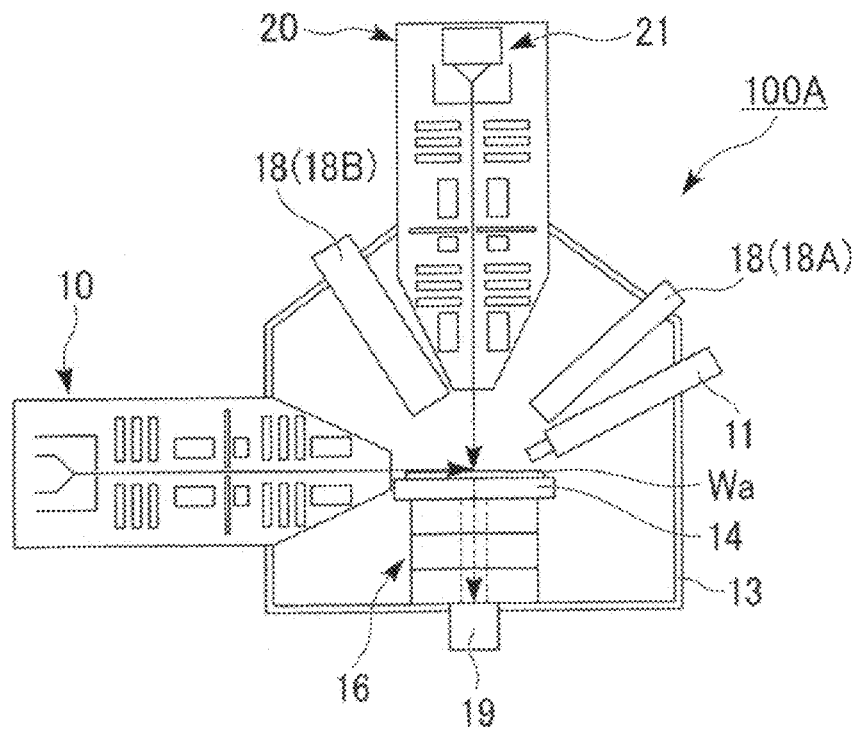
FIG. 4 is a diagram showing another configuration of the composite focused ion beam device according to the first embodiment.

FIG. 4 is a diagram showing a composite focused ion beam device 100A in which the dispositions of the first and second ion beam irradiation systems 10 and 20 are changed. In the composite focused ion beam device 100A shown in FIG. 4, the second ion beam irradiation system 20 is disposed on the vertical upper side of the sample Wa and the first ion beam irradiation system 10 is disposed on the lateral side of the sample Wa. The first ion beam 10A and the second ion beam 20A are emitted so as to be substantially orthogonal to each other.

As shown in FIG. 4, the first ion beam 10A and the second ion beam 20A are disposed so as to be substantially orthogonal to each other such that the processing of the sample using the first ion beam irradiation system 10 is performed while performing observation using the second ion beam irradiation system 20. Accordingly, the composite focused ion beam device 100A shown in FIG. 4 can be suitably used for the manufacture of a Transmission Electron Microscope (TEM) sample or the processing of a nano-order size atom probe or the like.

When a TEM sample is manufactured using the first ion beam irradiation system 10, it is possible to obtain a transmitted charged particle image using the second ion beam irradiation system 20 without driving the sample stage 16.

In addition, in the composite focused ion beam device 100A, the first ion beam irradiation system 10 and the second ion beam irradiation system 20 may be interchangeably disposed. Even in this case, the same effects can be obtained.

[Processing Observation Method and Processing Method]

Next, a processing observation method and a processing method using the composite focused ion beam device 100 according to the above embodiment will be described with reference to the drawings. The composite focused ion beam device 100 can be suitably used for analysis of a sample such as section processing observation of a sample, manufacture and observation of a Transmission Electron Microscope (TEM) sample and ion scattering spectrum, and sample processing such as formation of a minute structure to a sample and a wire changing process of an electronic device.

<Section Processing Observation and Sample Analysis>

FIG. 5 is a diagram showing a section processing observation method using the composite focused ion beam device 100. In addition, in FIG. 5, only a portion of the sample is shown in order to easily view the drawing.

In the processing observation method of the present example, while the sample Wa is consecutively processed using the first ion beam irradiation system 10, the section observation of the sample is performed by the irradiation of the second ion beam irradiation system 20 to the inner surface of the sample Wa exposed by the processing.

Figure 5A:
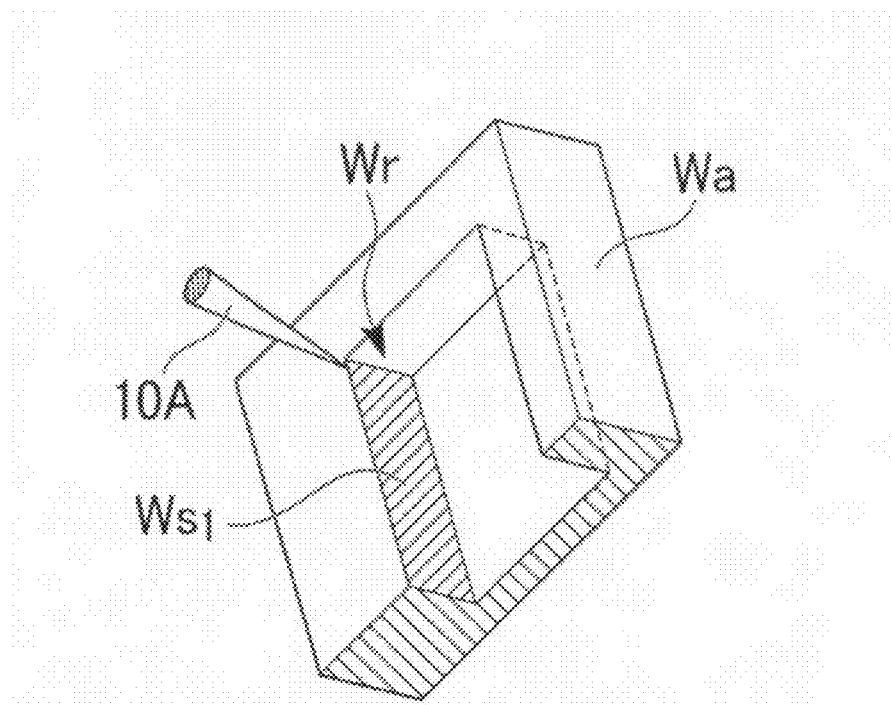
FIG. 5A is a diagram showing a section processing observation method which is an embodiment of a processing observation method.

First, as shown in FIG. 5A, the first ion beam 10A is scanned and irradiated to the surface of the sample Wa so as to partially remove the surface portion of the sample Wa, thereby forming a concave portion Wr having a rectangular shape. Accordingly, a measured surface Ws1 is exposed as an inner wall of the concave portion Wr.

Figure 5B:
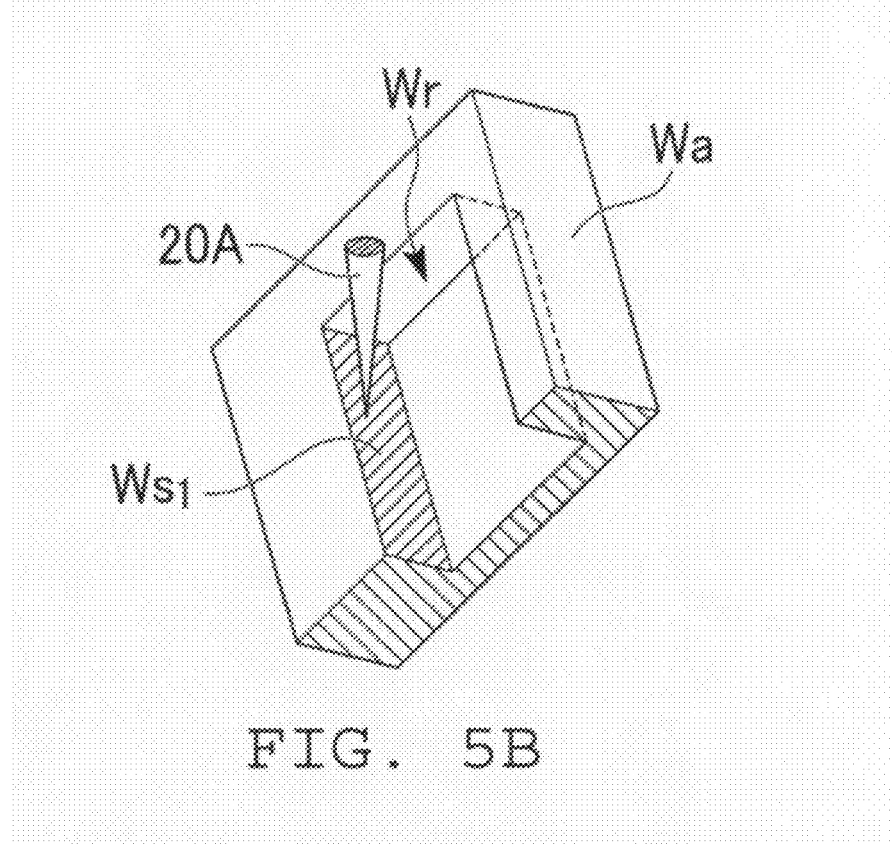
FIG. 5B is a diagram showing a section processing observation method which is an embodiment of a processing observation method.

In addition, as shown in FIG. 5B, the second ion beam 20A is irradiated to the formed measured surface Ws1. In addition, the generated secondary electrons or secondary ions are detected by the secondary charged particle detector 18, a sample image is displayed on the display device 38 based on the detected result, and section observation of a specific position of the sample Wa is performed.

Figure 5C:
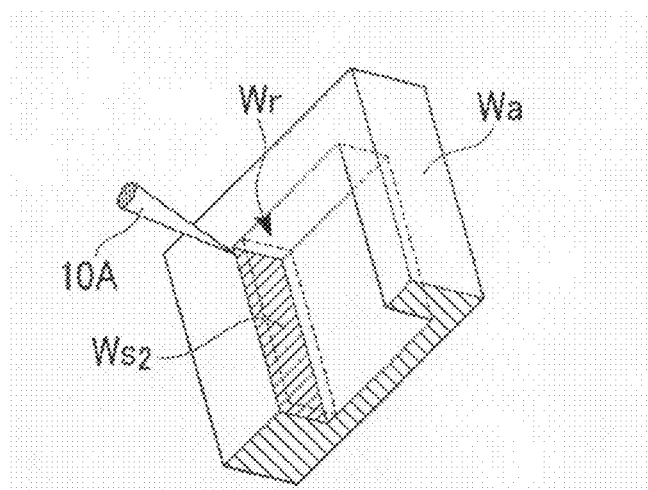
FIG. 5C is a diagram showing a section processing observation method which is an embodiment of a processing observation method.
Figure 5D:
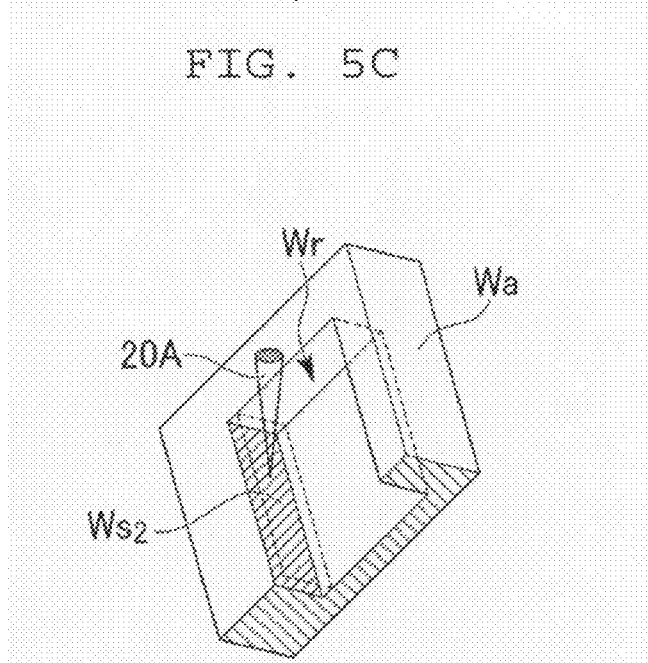
FIG. 5D is a diagram showing a section processing observation method which is an embodiment of a processing observation method.

Thereafter, when the processing using the first ion beam 10A is continuously performed, as shown in FIG. 5C, the structure of the inside of the measured surface Ws1 may be exposed as a measured surface Ws2. In addition, as shown in FIG. 5D, the second ion beam is irradiated to the measured surface Ws2 so as to obtain sample images having different sections.

Here, it is possible to simultaneously perform processing by the irradiation of the first ion beam 10A to the surface of the sample Wa and observation by the irradiation of the second ion beam 20A to the surface of the sample Wa which is being processed. That is, when the first ion beam 10A and the second ion beam 20A are simultaneously irradiated to the surface of the sample Wa, secondary ions or reflection ions are generated from the sample Wa by the irradiation of the first ion beam 10A and the second ion beam 20A. The reflection ions depend on the mass or the detection angle of the incident ion beam and thus can be easily distinguished from other detected particles. To this end, by detecting only the reflection ions from the sample by the second ion detector 18B during processing, it is possible to obtain a sample image with high resolution or high contrast. The simultaneous performing of the processing and the observation of the processed portion can improve processing precision since it can be accurately checked to which degree the sample is processed in real time.

Figure 5E:
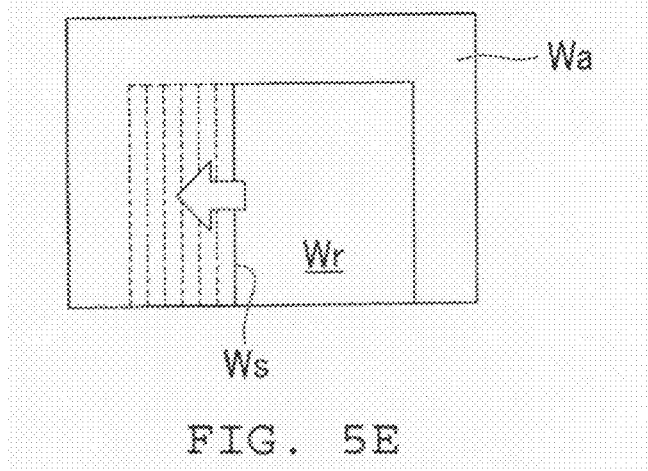
FIG. 5E is a diagram showing a section processing observation method which is an embodiment of a processing observation method.

As a schematic measurement process shown in FIG. 5E, in the processing observation method of the present example, it is possible to analyze, in detail, a section structure of a device formed in the sample Wa or the like, by continuously performing the processing of the sample Wa and the observation of the measured surfaces Ws (Ws1 and Ws2) exposed by the processing.

In the processing observation method of the present example, when the scattered ions generated by irradiating the second ion beam 20A to the sample Wa are detected and analyzed, it is possible to perform sample analysis (composition analysis) by ion scattering spectrum.

<TEM Sample Manufacture and Observation>

FIG. 6 is a diagram showing a processing observation method of a TEM sample using the composite focused ion beam device 100. In addition, in FIG. 6, only a portion of the sample is shown in order to easily view the drawing.

In the processing observation method of the present example, the first ion beam irradiation system 10 is used for the processing of the sample Wa or the sample Wb and the second ion beam irradiation system 20 is used for the observation of the processed sample Wa or the sample Wb.

Figure 6A:
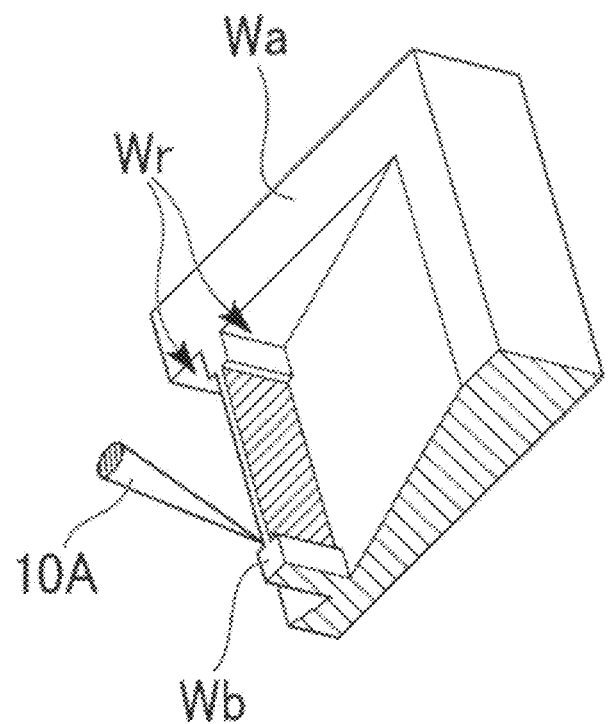
FIG. 6A is a diagram showing a TEM sample manufacturing and observation method which is an embodiment of a processing observation method.

First, as shown in FIG. 6A, the first ion beam 10A is scanned and irradiated to the surface of the sample Wa so as to partially remove the surface portion of the sample Wa and concave portions Wr and Wr including a bottom surface having a slope shape are formed at both sides of the sample Wb which is the TEM sample. Thereafter, the sample Wb is detached from the sample Wa in a state of being supported by the manipulator 17 and the detached sample Wb is moved to the sample holder 15 by the manipulator 17.

Figure 6B:
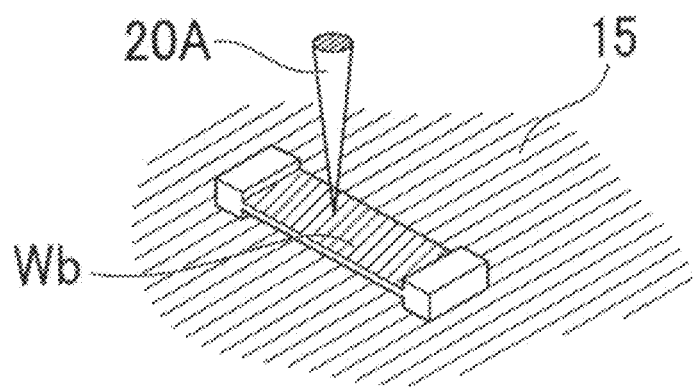
FIG. 6B is a diagram showing a TEM sample manufacturing and observation method which is an embodiment of a processing observation method.

In addition, as shown in FIG. 6B, by irradiating the second ion beam 20A to the sample Wb on the sample holder 15, the transmitted ions may be detected by the transmitted charged particle detector 19 and a sample image (transmitted charged particle image) may be displayed on the display device 38 based on the detected result.

Next, in the processing observation method of the present example, in the processing step of the sample Wa shown in FIG. 6A, the first ion beam irradiation system 10 and the second ion beam irradiation system 20 may be simultaneously used. Since the second ion beam irradiation system 20 may irradiate the second ion beam 20A having a beam diameter less than that of the first ion beam irradiation system 10, a method of performing rough processing with respect to a peripheral portion of a portion which becomes the TEM sample using the first ion beam 10A and performing finishing processing of the TEM sample using the second ion beam irradiation system 20 and the gas gun 11 may be used.

In the processing using the second ion beam 20A, since the beam diameter is narrowed as compared with the first ion beam 10A, it is possible to concentrically irradiate the beam to a portion to be cut. To this end, high-precision processing which cannot be obtained in the processing by the irradiation of the first ion beam 10A is possible.

In addition, in the processing using the second ion beam 20A, since the mass of the second ions is less than that of the first ion beam 10A, damage to the sample, such as a problem that the irradiated ions are left in the sample without conversion, is hardly caused. To this end, by irradiating the second ion beam 20A in an etching gas atmosphere from the gas gun 11, it is possible to easily remove a damaged portion left in the sample when irradiating the first ion beam 10A in advance. As a result, it is possible to manufacture a TEM sample with a small damaged portion.

Figure 7:
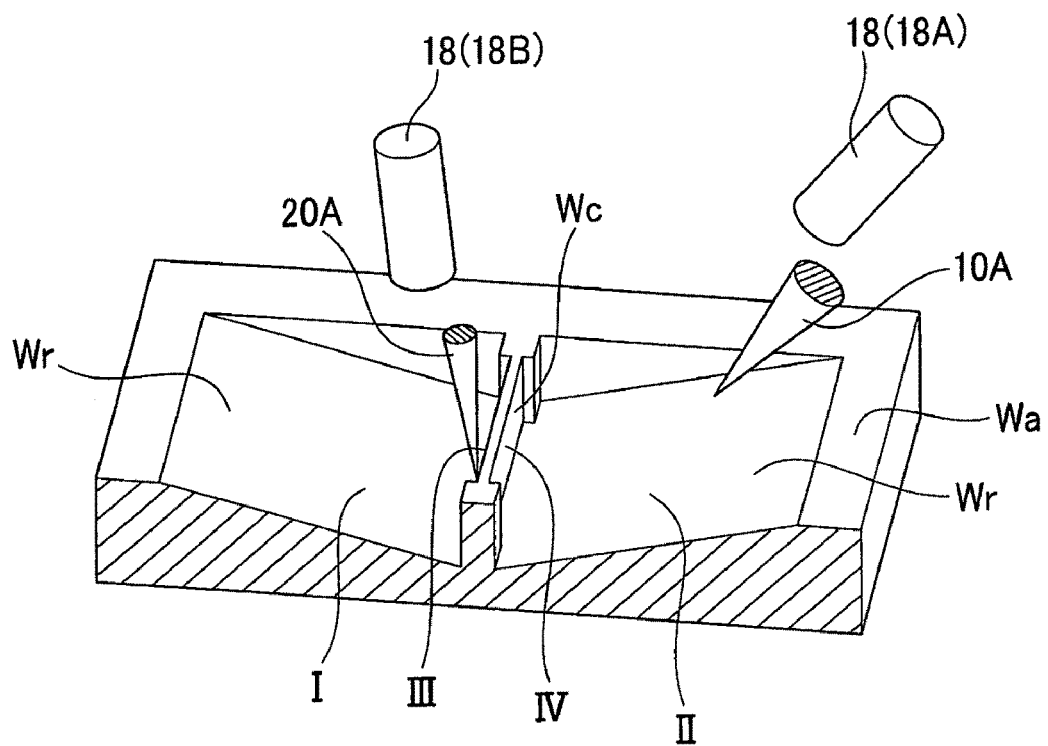
FIG. 7 is a diagram showing a TEM sample manufacturing method which is an embodiment of a processing method.

FIG. 7 is a diagram showing a procedure of manufacturing a TEM sample. Here, first, a concave portion Wr (denoted by I in the drawing) having a slope shape at the left side of FIG. 7 is removed by irradiating the first ion beam 10A. Next, a concave portion Wr (denoted by II in the drawing) having a partially slope shape at the right side of FIG. 7 is removed by irradiating the first ion beam. Simultaneously, a portion (denoted by III in the drawing) adjacent to a portion Wc which becomes the TEM sample of the concave portion Wr having the slope shape at the removed left side is removed by irradiating the second ion beam 20A. Next, a portion (denoted by IV in the drawing) adjacent to the portion Wc which becomes the TEM sample of the concave portion Wr having the slope shape at the removed right side is removed by irradiating the second ion beam 20A.

That is, in this TEM sample manufacturing method, in second processing, rough processing of removing the concave portion Wr (denoted by II in the drawing) having the partially slope shape at the right side and finishing processing of removing the portion adjacent to the portion Wc which becomes the TEM sample of the concave portion Wr having the slope shape at the removed left side are simultaneously performed and thus processing efficiency can be improved. At this time, there may be a problem that the material removed when the rough processing is performed is reattached to the finishing processed portion. However, since the portion Wc which becomes the TEM sample is present between both the processed regions, such a problem does not easily occur. When the rough processing and the finishing processing are simultaneously performed, the secondary ions generated by the irradiation of the first ions can be detected by the first ion detector 18A and the reflection ions reflected by collision of the second ions with the sample can be detected by the second ion detector 18B. Thus, the processed portions can be simultaneously monitored. Even in this case, processing efficiency can be improved.

Figure 8:
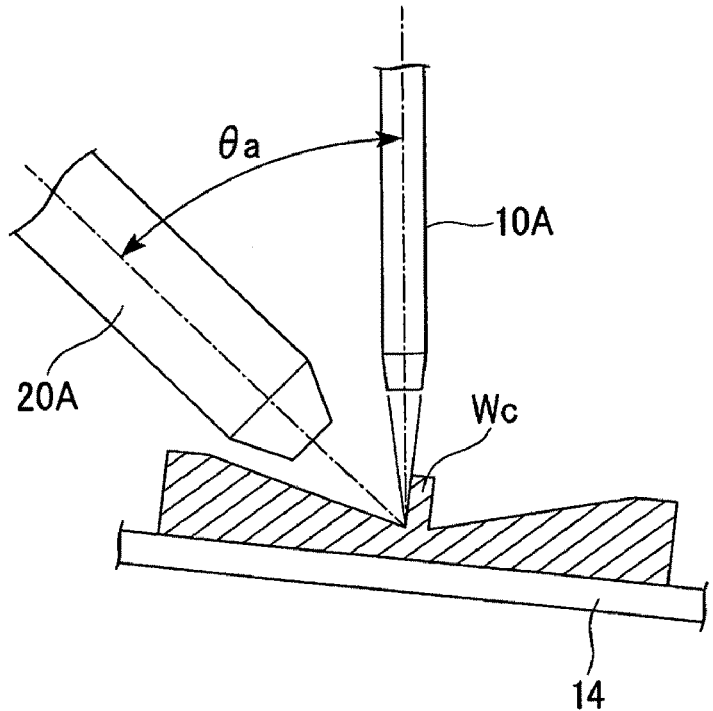
FIG. 8 is a diagram showing a TEM sample manufacturing method which is an embodiment of a processing method.
Figure 9:
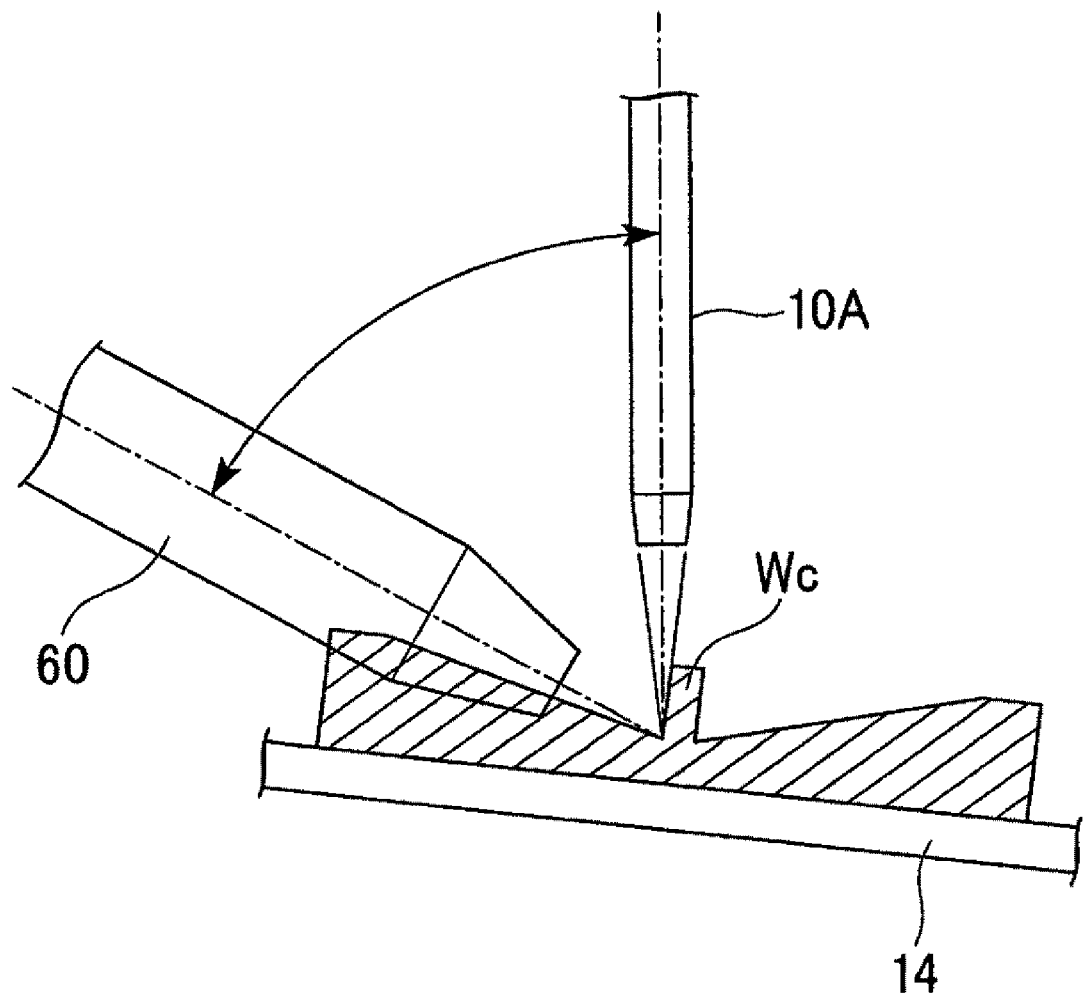
FIG. 9 is a diagram showing a TEM sample manufacturing method which is an example of a processing method.

FIGS. 8 and 9 are diagrams illustrating processed states when the portion adjacent to the portion Wc which becomes the TEM sample is removed in the TEM sample manufacturing process. These drawings show the relative relationship among the first ion beam irradiation system 10, the second ion beam irradiation system 20 and the sample pedestal 14. In these drawings, the first ion beam irradiation system 10 is directed in a vertical direction of the drawing.

Here, the first ion beam irradiation system 10 and the second ion beam irradiation system 20 are disposed such that the angle θa between the axes thereof becomes 45 degrees to 60 degrees. Originally, the reason why the first ion beam irradiation system 10 and the second ion beam irradiation system 20 may be disposed such that the opened angle θa becomes 45 degrees to 60 degrees is because the diameter of the front end of the beam lens barrel of the second ion beam irradiation system 20 is less than that of the lens barrel of the SEM. That is, for example, if an SEM 60 is disposed instead of the second ion beam irradiation system 20, as shown in FIG. 9, since the front end of the lens barrel of the SEM 60 has a magnetic field lens generation coil, the diameter thereof is greater than that of the second ion beam irradiation system 20. In case of the SEM, a Working Distance (WD) may not be set to be large. To this end, if the SEM 60 and the first ion beam irradiation system 10 are disposed, the opened angle therebetween necessarily becomes an angle (for example, 65 degrees) greater than 60 degrees. If the opened angle between both lens barrels is increased, the following problems occur.

That is, if the vicinity of the portion Wc which becomes the TEM sample is processed using the first ion beam 10A, the processing needs to be performed by decreasing the beam current so as not to cause damage to the sample as much as possible. In this case, as the beam current is decreased, the beam diameter is increased and thus the sample needs to be tilted due to the large beam diameter. That is, the sample pedestal needs to be sufficiently tilted. However, if the SEM 60 and the first ion beam irradiation system 10 are disposed, the opened angle therebetween is increased. Thus, a phenomenon that the sample pedestal and the lens barrel interfere with each other occurs and thus the inclination angle (tilt angle) of the sample pedestal may not be set to be large. That is, in FIG. 8, if the sample pedestal is inclined upward to the right, the sample pedestal can be inclined at a relatively large angle, but, if the sample pedestal is inclined upward to the left, the sample pedestal or the sample laid on the sample pedestal and the SEM lens barrel interfere with each other and the inclination angle of the sample pedestal may not be set to be large. In order to avoid this problem, after the sample pedestal is inclined upward to the right and one side of the portion Wc which becomes the TEM sample is removed and processed, the sample pedestal is rotated by 180 degrees and the opposite side of the portion Wc which becomes the TEM sample is removed and processed. In this case, a positioning operation should be performed with respect to the sample on the sample pedestal and this operation is very troublesome.

If the first ion beam irradiation system 10 and the second ion beam irradiation system 20 are combined like the above-described embodiment, the angle θa between the axes thereof may be set to a relatively narrow range of 45 degrees to 60 degrees and thus the left and right inclination angle of the sample pedestal 14 may not be set to be large. To this end, the left and right sides of the portion We which becomes the TEM sample may be processed by the low beam current using the first ion beam 10A without rotating the sample pedestal by 180 degrees.

<Formation of Minute Structure>

FIG. 10 is a diagram showing a minute structure forming method (processing method) to a sample according to the composite focused ion beam device 100.

In the processing method of the present example, the first ion beam irradiation system 10, the second ion beam irradiation system 20 and the gas gun 11 are used for the processing of a minute structure to the sample Wa or the sample Wb.

Figure 10A:
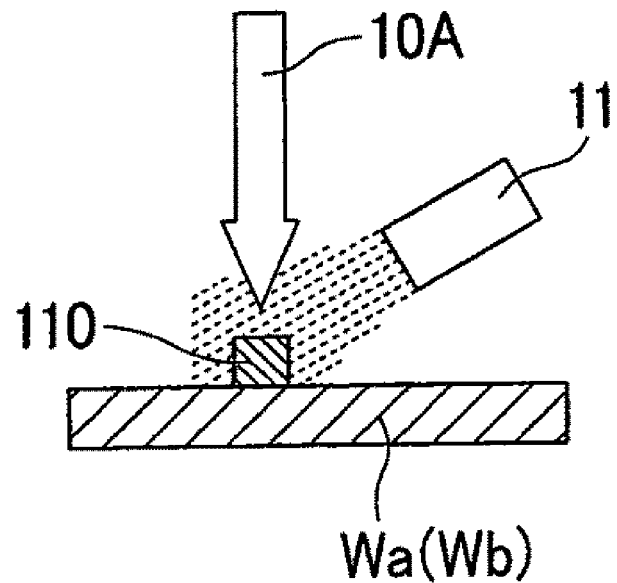
FIG. 10A is a diagram showing a minute structure forming method which is an embodiment of a processing method.
Figure 10B:
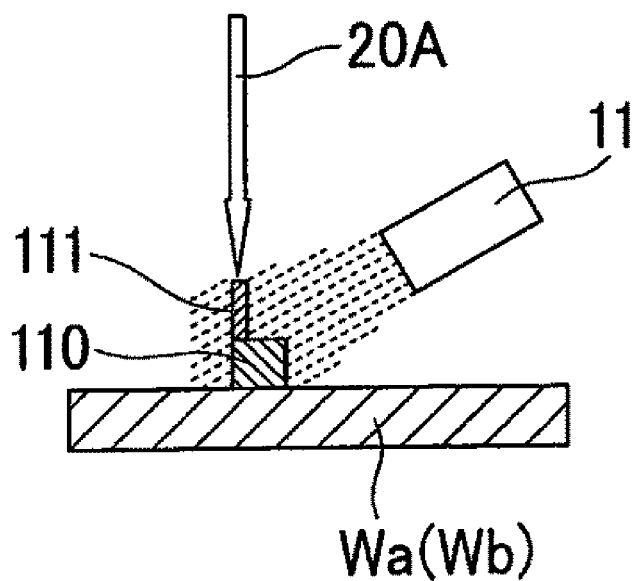
FIG. 10B is a diagram showing a minute structure forming method which is an embodiment of a processing method.

First, as shown in FIG. 10A, the first ion beam 10A is irradiated while deposition gas is blown from the gas gun 11 onto the sample Wa or the sample Wb so as to form a first structure 110 formed of, for example, carbon or metal. Next, as shown in FIG. 10B, the second ion beam 20A is irradiated while deposition gas is blown from the gas gun 11 onto the first structure 110 so as to form a second structure 111 on the first structure 110. By using the second ion beam 20A, it is possible to manufacture the structure 111 without mixing the first ion (for example, gallium ions).

According to the composite focused ion beam device 100 of the present embodiment, it is possible to form a minute structure by combining deposition using the first ion beam 10A having a large beam diameter and deposition using the second ion beam 20A having a small beam diameter. Accordingly, it is possible to efficiently form the first structure 110 having a relatively large size and to easily and accurately form the second structure 111 having a minute size, which cannot be formed by the first ion beam irradiation system 10.

Although the formation of the minute structure by the gas assist deposition is shown in FIG. 10, sputtering using the first ion beam 10A and the gas assist etching using the second ion beam 20A may be combined, if necessary. Accordingly, according to the minute structure forming method of the present example, it is possible to rapidly and accurately form a minute structure having a desired shape.

As another processing method, mainly, a method of observing a structure using the second ion beam irradiation system 20 while forming the structure using the first ion beam irradiation system 10 may be employed. If such a processing method is used, since the minute process can be performed while the finished state of the structure is checked, it is possible to form a minute structure with excellent product yield. This processing method is suitably used in the manufacture (etching processing) of an atom probe requiring an extremely sharp front end shape.

<Wire Change>

FIG. 11 is a diagram showing a wire changing method (processing method) of an IC or the like using the composite focused ion beam device 100.

In the processing method of the present example, the first ion beam irradiation system 10, the second ion beam irradiation system 20 and the gas gun 11 are used for the wire change of an electronic circuit 120.

Figure 11A:
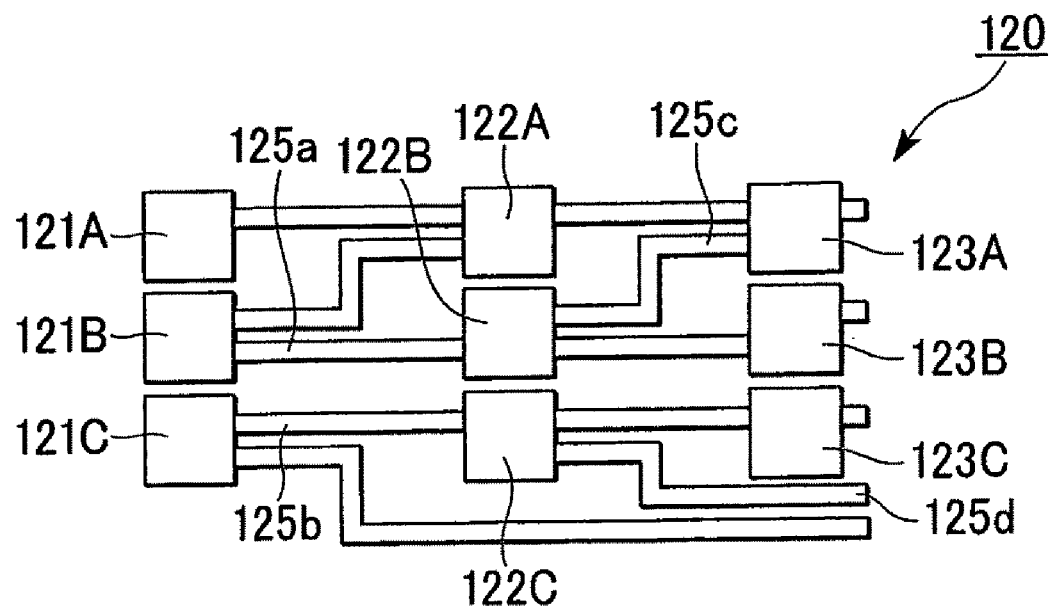
FIG. 11A is a diagram showing a wire changing method which is an embodiment of a processing method.

The electronic circuit 120 shown in FIG. 11A includes logic circuits 121A to 121C, 122A to 122C and 123A to 123C and a wire group for connecting the circuits. The wire to be processed of the present example includes a wire 125a for connecting the logic circuits 121B and 122B, a wire 125b for connecting the logic circuits 121C and 122C and a wire 125c for connecting the logic circuits 122B and 123A.

The wire changing method of the present example has a wire cutting process for cutting the existing wire, and a rewiring process for changing a connection path of a wire.

Figure 11B:
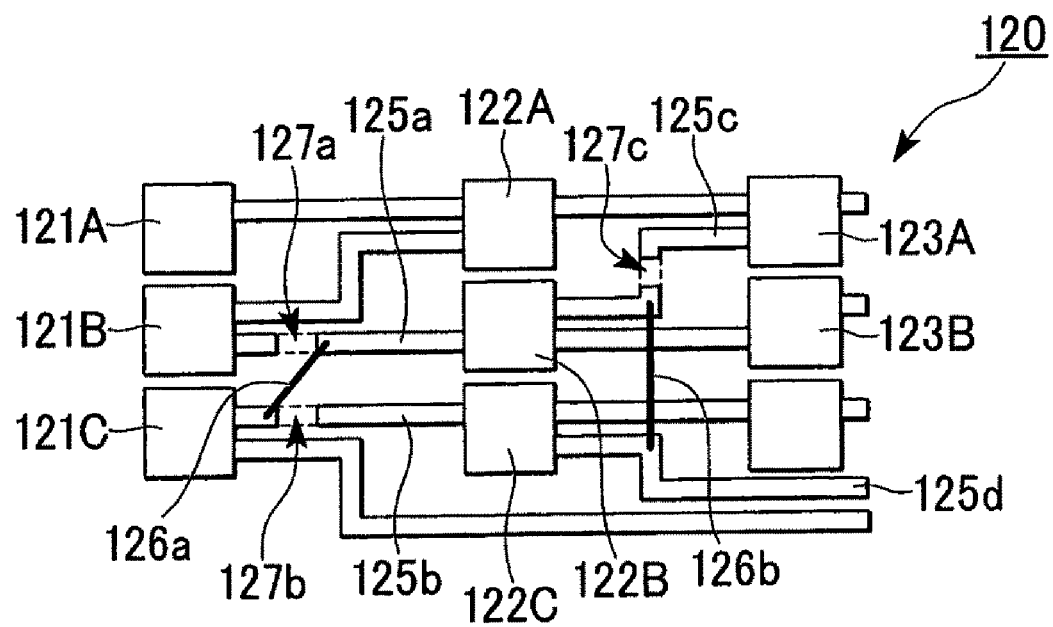
FIG. 11B is a diagram showing a wire changing method which is an embodiment of a processing method.

First, in the wire cutting process, as shown in FIG. 11B, the first ion beam 10A is irradiated to a cut portion 127a of the wire 125a, a cut portion 127b of the wire 125b and a cut portion 127c of the wire 125c so as to cut the wires.

In the wire cutting process, the processing may be performed while the processed state by the first ion beam 10A is observed using the second ion beam irradiation system 20. By performing such a processing method, it is possible to accurately perform the wire cutting process. In particular, if the helium ion beam is used as the second ion beam 20A, it is possible to avoid the surface of the sample (electronic circuit 120) from being sputtered.

The wire cutting process may be performed by gas assist etching using the second ion beam irradiation system 20 and the gas gun 11 or the irradiation of the second ion beam 20A formed of argon ions. In addition, the first ion beam irradiation system 10 and the second ion beam irradiation system 20 may be simultaneously used. That is, a relatively large region may be processed using the first ion beam 10A and a minute region may be processed using the second ion beam irradiation system 20.

Meanwhile, in the rewiring process, the first ion beam 10A is irradiated while gas including a wire forming material is blown from the gas gun 11 such that a portion of the logic circuit 122B side in the cut wire 125a and a portion of the logic circuit 121c side in the wire 125b are connected, thereby forming a wire 126a.

In addition, the first ion beam 10A is irradiated while gas including a wire forming material is blown from the gas gun 11 such that a portion of the logic circuit 122B side in the cut wire 125c and the wire 125d extending from the logic circuit 122C are connected, thereby forming a wire 126b.

In the rewiring process, the processing may be performed while the processed state by the first ion beam 10A is observed using the second ion beam irradiation system 20. By performing such a processing method, it is possible to accurately perform the rewiring process.

In the rewiring process, the second ion beam 20A may be used instead of the first ion beam 10A. That is, it is possible to form the wires 126a and 126b by the gas assist deposition using the second ion beam irradiation system 20 and the gas gun 11.

Even in the rewiring process, the first ion beam irradiation system 10 and the second ion beam irradiation system 20 may be simultaneously used. That is, a relatively large region may be processed using the first ion beam 10A and a minute region may be processed using the second ion beam irradiation system 20.

Second Embodiment

Next, a second embodiment of the present invention will be described with reference to FIG. 12.

Figure 12:
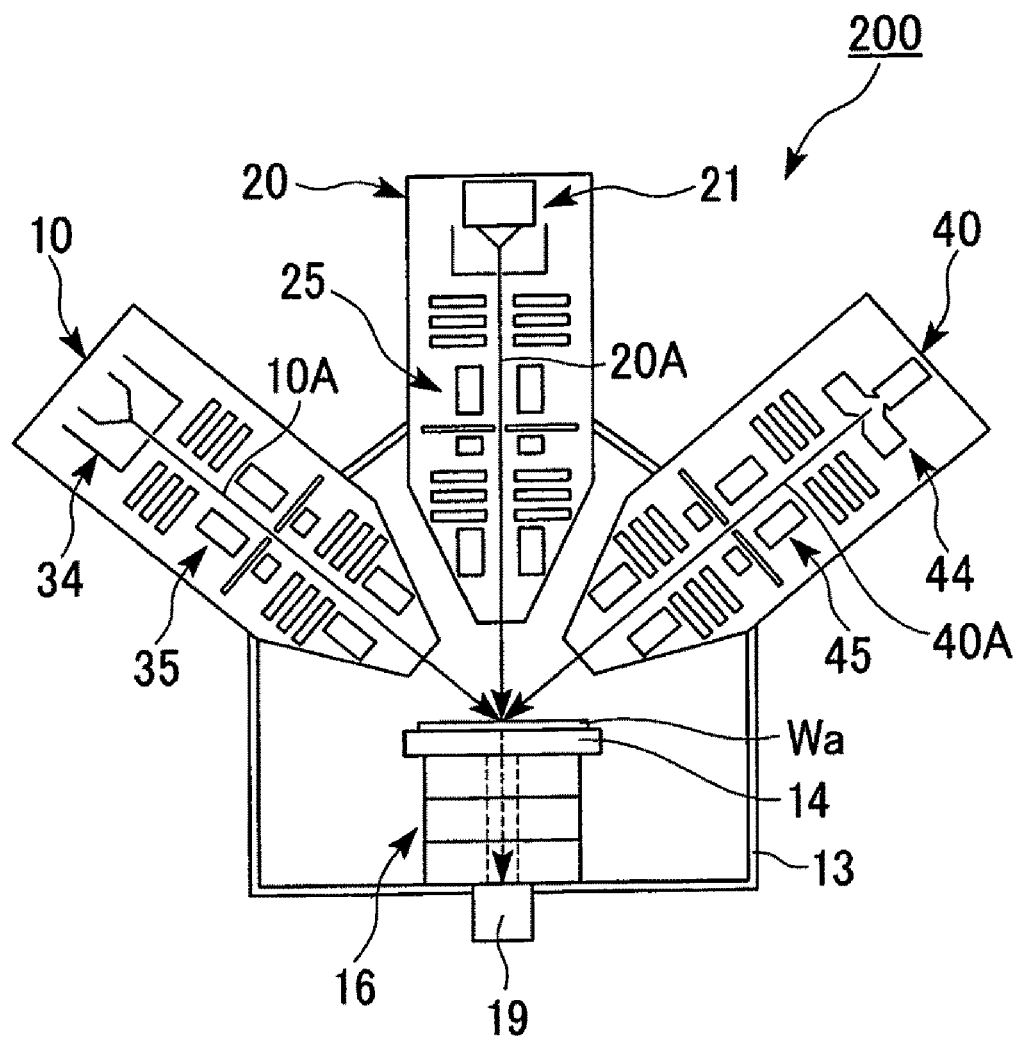
FIG. 12 is a schematic cross-sectional view of a composite focused ion beam device according to a second embodiment.

FIG. 12 is a schematic cross-sectional view of composite focused ion beam device 200 according to the present embodiment. In addition, in FIG. 12, the same components as FIGS. 1 to 3 are denoted by the same reference numerals and detailed description thereof will be omitted.

First, as shown in FIG. 12, the composite focused ion beam device 200 according to the present embodiment includes a third ion beam irradiation system 40 for emitting a third ion beam 40A, in addition to the first ion beam irradiation system 10 and the second ion beam irradiation system 20. The ion beam irradiation systems 10, 20 and 40 are fixed to the vacuum chamber 13 so as to irradiate the first ion beam 10A, the second ion beam 20A and the third ion beam 40A emitted therefrom to the sample Wa (or the sample Wb).

The third ion beam irradiation system 40 includes a plasma type gas ion source 44 and an ion optical system 45. The plasma type gas ion source 44 includes, for example, a plasma generator for emitting a third ion while maintaining plasma therein, an extraction orifice for extracting the third ion from the plasma generator, and an extraction electrode for electrostatically accelerating the third ion passing the extraction orifice.

Rare gas is used in plasma gas which forms plasma in the plasma type gas ion source 44. That is, plasma gas is preferably one or plural types of gas selected from neon, argon, xenon and krypton and, among them, argon or xenon are more preferably used.

The third ions extracted from the extraction electrode are emitted in a beam form and are focused by performing an ion optical operation by the ion optical system 45 such that a focused ion beam (third ion beam) 40A is irradiated to a sample Wa.

Figure 13:
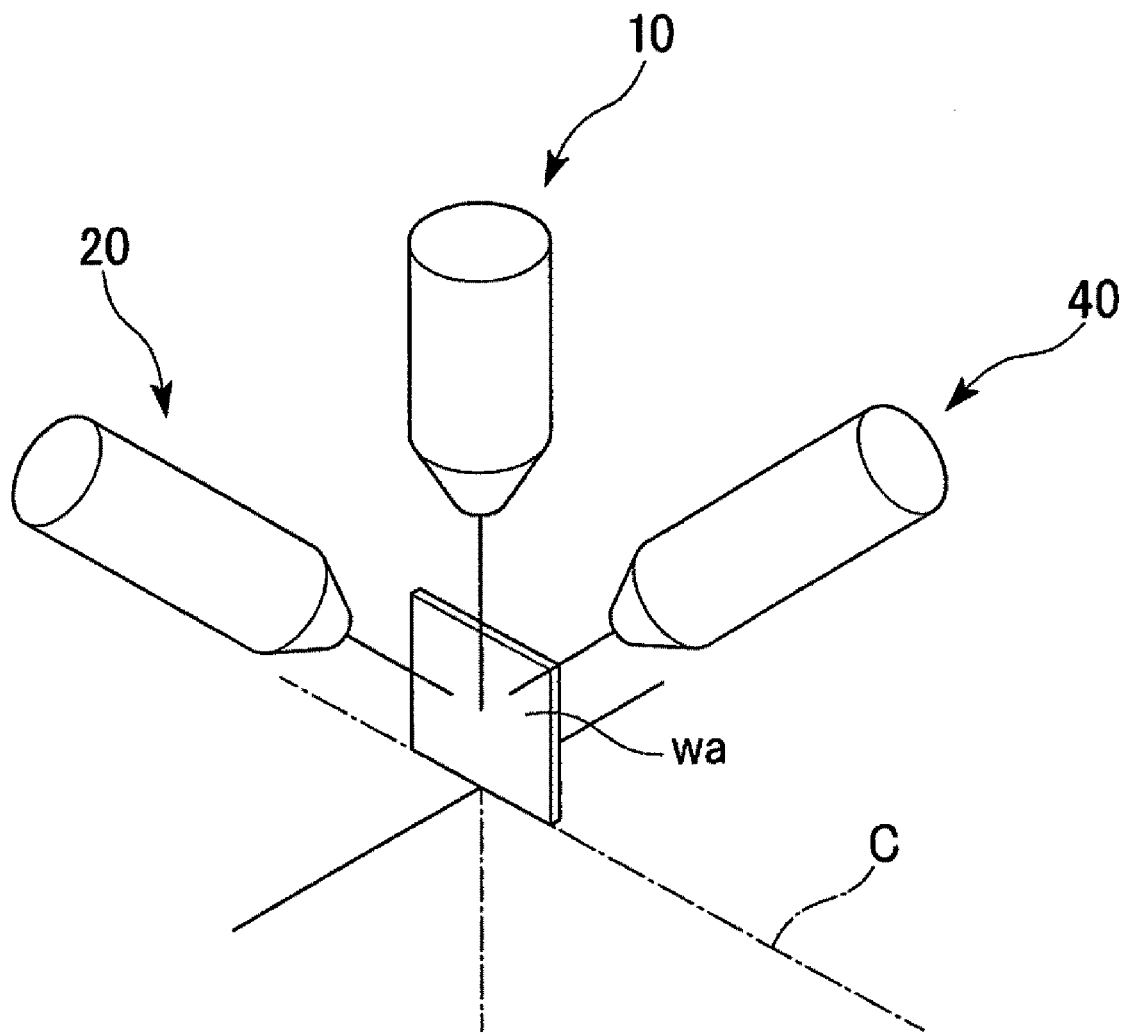
FIG. 13 is a schematic perspective view showing a disposition example of first, second and third ion beams.

The first ion beam irradiation system 10, the second ion beam irradiation system 20 and the third ion beam irradiation system 40 are disposed such that the axes of the first ion beam irradiation system 10 and the second ion beam irradiation system 20 are orthogonal to a stage tilt axis C and the axis of the third ion beam irradiation system 40 and the stage tilt axis C are located in the same plane, as shown in FIG. 13.

The ion optical system 45 includes, for example, a condenser lens for focusing an ion beam, a diaphragm for narrowing the ion beam, an aligner for adjusting an optical axis of the ion beam, an objective lens for focusing the ion beam to a sample, and a deflector for scanning the ion beam on the sample, sequentially from the plasma type gas ion source 44 to the vacuum chamber 13.

The composite focused ion beam device 200 according to the present embodiment having the above configuration is a composite focused ion beam device which can perform more various observation and processing procedures than those of the first embodiment, by including the third ion beam irradiation system 40 in addition to the first ion beam irradiation system 10 and the second ion beam irradiation system 20, in addition to the same analysis and processing of the sample as the composite focused ion beam device 100 according to the first embodiment.

For example, by cleaning the sample surface using the third ion beam irradiation system 40 after the processing using the first ion beam irradiation system 10 including the liquid metal ion source 34, it is possible to remove gallium ions or the like implanted into the sample by the irradiation of the first ion beam 10A.

In the manufacture of the TEM sample, the minute sample Wb may be cut from the large sample Wa using the first ion beam irradiation system 10 and the cut sample Wb may be subjected to the finishing processing using the first ion beam irradiation system 10 or the second ion beam irradiation system 20. At this time, the finished state may be observed using the second ion beam irradiation system 20. By cleaning the damaged portion due to the irradiation of the liquid metal ions to the completed sample Wb using the third ion beam irradiation system 40, it is possible to manufacture a TEM sample with a small damaged portion.

Since the first ion beam irradiation system 10, the second ion beam irradiation system 20 and the third ion beam irradiation system 40 are disposed such that the axes of the first ion beam irradiation system 10 and the second ion beam irradiation system 20 are orthogonal to the stage tilt axis C and the axis of the third ion beam irradiation system 40 and the stage tilt axis C are located in the same plane, it is possible to easily set the angle of the ion beam irradiated from each of the ion beam irradiation systems with the sample and to improve a processing property.

In the first wire changing method, if the cleaning process using the third ion beam irradiation system 40 or the refilling of a hole formed in an insulating film at the same time of processing may be performed after the processing using the first ion beam irradiation system 10, it is possible to perform a sample recovering process while removing the implanted ions by the first ion beam 10A.

The present invention relates to a composite focused ion beam device. According to the composite focused ion beam device of the present invention, since a first ion beam irradiation system having a liquid metal ion source for generating a first ion and a second ion beam irradiation system including a gas field ion source for generating a second ion are included and a beam diameter of the second ion beam emitted from the second ion beam irradiation system is less than that of the first ion beam emitted from the first ion beam irradiation system, it is possible to perform super-high-resolution observation or super-high-precision processing which is impossible by the conventional composite focused ion beam device or composite charged particle beam device.

The invention claimed is:

1. A composite focused ion beam device comprising:
   a first ion beam irradiation system that irradiates a first ion beam for processing a sample and having a first beam diameter, the first ion beam irradiation system having a liquid metal ion source that generates first ions for forming the first ion beam; and
   a second ion beam irradiation system that irradiates a second ion beam for processing or observing the sample and having a second beam diameter smaller than the first beam diameter, the second ion beam irradiation system having a gas field ion source that generates second ions for forming the second ion beam; and
   a sample stage for supporting the sample, the first and second ion beam irradiation systems being disposed relative to the sample stage so that axes of the first and second ion beams are orthogonal to a tilt axis of the sample stage.

2. A composite focused ion beam device according to claim 1; wherein a mass of the second ion is less than that of the first ion.

3. A processing and observation method of a sample, the method comprising the steps of:
   providing a composite focused ion beam device comprising a sample stage for supporting a sample and mounted for undergoing tilting movement, a first ion beam irradiation system having a liquid metal ion source that generates first ions for forming a first ion beam, and a second ion beam irradiation system having a gas field ion source that generates second ions for forming a second ion beam, the first and second ion beam irradiation systems being disposed relative to the sample stage so that axes of the first and second ion beams are orthogonal to a tilt axis of the sample stage;

processing the sample by irradiating the sample with the first ion beam from the first ion beam irradiation system, the first ion beam having a first beam diameter; and observing the sample by irradiating the sample with the second ion beam from the second ion beam irradiation system, the second ion beam having a second beam diameter smaller than the first beam diameter.

4. A processing and observation method according to claim 3; wherein the step of irradiating the first ion beam for processing the sample and the step of irradiating the second ion beam for observing the sample are performed simultaneously.

5. A processing method of a sample, the processing method comprising the steps of:

providing a composite focused ion beam device comprising a sample stage for supporting a sample and mounted for undergoing tilting movement, a first ion beam irradiation system having a liquid metal ion source that generates first ions for forming a first ion beam, and a second ion beam irradiation system having a gas field ion source that generates second ions for forming a second ion beam, the first and second ion beam irradiation systems being disposed relative to the sample stage so that axes of the first and second ion beams are orthogonal to a tilt axis of the sample stage;

processing the sample by irradiating the sample with the first ion beam from the first ion beam irradiation system, the first ion beam having a first beam diameter; and processing the sample by irradiating the sample with the second ion beam from the second ion beam irradiation system, the second ion beam having a second beam diameter smaller than the first beam diameter.

6. A processing method of a sample, the processing method comprising the steps of:

providing a composite focused ion beam device comprising a sample stage for supporting a sample and mounted for undergoing tilting movement, a first ion beam irradiation system having a liquid metal ion source that generates first ions for forming a first ion beam, and a second ion beam irradiation system having a gas field ion source that generates second ions for forming a second ion beam, the first and second ion beam irradiation systems being disposed relative to the sample stage so that axes of the first and second ion beams are orthogonal to a tilt axis of the sample stage;

performing processing of the sample by irradiating the sample with the first ion beam from the first ion beam irradiation system, the first ion beam having a first beam diameter; and performing finish processing of the sample by irradiating at least a portion of the sample processed by the first ion beam irradiation system with the second ion beam from the second ion beam irradiation system, the second ion beam having a second beam diameter smaller than the first beam diameter.

7. A processing method according to claim 6; wherein the steps of irradiating the sample with the first ion beam and the second ion beam are simultaneously performed.

8. A composite focused ion beam device according to claim 1; wherein the first ion beam irradiation system and the second ion beam irradiation system are mounted so that the first ion beam and the second ion beam cross each other at an acute angle.

9. A composite focused ion beam device according to claim 8; further comprising a sample pedestal mounted on the sample stage for supporting the sample; and wherein the second ion beam irradiation system extends in a vertical direction relative to an upper side of the sample pedestal and the first ion beam irradiation system is disposed obliquely to the vertical direction.

10. A composite focused ion beam device according to claim 8; wherein the acute angle is in the range of 45 degrees to 60 degrees.

11. A composite focused ion beam device according to claim 1; wherein the first and second ion beam irradiation systems are mounted so that the first and second ion beams are substantially orthogonal to each other.

12. A composite focused ion beam device according to claim 1; further comprising a third ion beam irradiation system that irradiates a third ion beam for processing a sample, the third ion beam irradiation system having a plasma type gas ion source for generating third ion that is converted into the third ion beam.

13. A composite focused ion beam device according to claim 12; wherein a mass of the third ion generated by the plasma type gas ion source is greater than that of the second ion generated by the gas field ion source.

14. A composite focused ion beam device according to claim 12; wherein an axis of the third ion beam irradiation system and the tilt axis of the sample stage are located on a common plane of the sample.

15. A composite focused ion beam device according to claim 1; further comprising a detection device for detecting at least one of a secondary charged particle generated or reflected from the sample by the irradiation of the first ion or the second ion and a charged particle transmitted through the sample, and an image display device for displaying an image of the sample based on an output of the detection device.

16. A composite focused ion beam device according to claim 15; wherein the detection device comprises at least one of an electron detector, an ion detector, and a transmitted charged particle detector.

17. A processing and observation method according to claim 3; wherein the irradiation of the first and second ion beams are simultaneously performed.

18. A processing and observation method according to claim 3; wherein the providing step further comprises providing a third ion beam irradiation system having a plasma type gas ion source for generating a third ion that is converted into a third ion beam; and further comprising the step of irradiating the sample with the third ion beam after the step of irradiating the sample with the first ion beam.

19. A processing and observation method according to claim 3; wherein the providing step further comprises providing a third ion beam irradiation system having a plasma type gas ion source for generating a third ion that is converted into a third ion beam; and further comprising the steps of irradiating the sample with the third ion beam so as to cut a minute sample portion from the sample and irradiating the cut minute sample portion with the first ion beam to process the minute sample portion.

* * * * *